United States Patent
Schutyser et al.

(10) Patent No.: US 9,439,608 B2
(45) Date of Patent: Sep. 13, 2016

(54) METHOD FOR DERIVING SHAPE INFORMATION

(75) Inventors: Filip Schutyser, Sint-Niklaas (BE); Pieter De Groeve, Brussels (BE); Tinne Van Delm, Beerse (BE); Wouter Mollemans, Mechelen (BE); Kevin Suestens, Bonheiden (BE); Gwen Swennen, Knokke-Heist (BE); Nasser Nadjmi, Antwerpen (BE)

(73) Assignee: MEDICIM NV, Mechelen (BE)

( * ) Notice: Subject to any disclaimer, the term of this patent is extended or adjusted under 35 U.S.C. 154(b) by 886 days.

(21) Appl. No.: 12/596,829

(22) PCT Filed: Apr. 18, 2008

(86) PCT No.: PCT/EP2008/003135
§ 371 (c)(1),
(2), (4) Date: Nov. 30, 2010

(87) PCT Pub. No.: WO2008/128720
PCT Pub. Date: Oct. 30, 2008

(65) Prior Publication Data
US 2011/0059413 A1    Mar. 10, 2011

(30) Foreign Application Priority Data

Apr. 20, 2007 (EP) .................................... 07106650

(51) Int. Cl.
*A61C 3/00* (2006.01)
*A61B 6/14* (2006.01)
(Continued)

(52) U.S. Cl.
CPC .............. *A61B 6/14* (2013.01); *A61B 5/1077* (2013.01); *A61B 5/4547* (2013.01);
(Continued)

(58) Field of Classification Search
CPC .... A61C 9/0053; A61C 9/004; A61C 9/006; A61C 13/081; A61C 7/002; A61C 9/0046; A61C 19/05; A61C 11/00; A61C 3/00; A61C 9/00; A61B 5/1077; A61B 5/4547; A61B 5/4504; A61B 17/666; A61B 17/80; A61B 19/50; A61B 6/5229–6/5247; A61B 6/501; A61B 6/505; A61B 6/14; A61B 6/145; A61B 6/032; G06T 7/0022–7/0038; G06T 2207/10081; G06T 2211/40; G01B 9/0209; G01B 9/02091; G01N 23/046; G01V 5/005; G05B 2219/45166
USPC .......... 433/7, 8, 140, 24; 703/1, 3; 382/128, 382/131; 600/425; 378/98.12, 38–40, 4, 19; 250/363.01–363.02; 356/479, 497
See application file for complete search history.

(56) References Cited

U.S. PATENT DOCUMENTS

| | | | |
|---|---|---|---|
| 4,155,163 A | * | 5/1979 | Schwartz ............... A61C 11/02 433/56 |
| 4,836,778 A | | 6/1989 | Baumrind et al. |

(Continued)

FOREIGN PATENT DOCUMENTS

| | | |
|---|---|---|
| DE | 3522196 | 2/1986 |
| EP | 1 542 165 | 6/2002 |

(Continued)

OTHER PUBLICATIONS

"Radiation Dose Considerations in CT Imaging" by Jeffrey T. Seabourn, M.D. from Gem State Radiology—http://bluecoat-02/?cfru=aHR0cDovL3d3dy5pbWlyYWQubmV0L1BSRVNFTIRBVEIPTIMvUkFESUFUSU9OJTIwRE9TRSUyMENPTINJREVSQVRJT05TJTIwSUfIMjBDVCUyMEINQUdJTkcIMjAyMDEwLn BwdA==.*

(Continued)

*Primary Examiner* — Cris L Rodriguez
*Assistant Examiner* — Mirayda A Aponte
(74) *Attorney, Agent, or Firm* — Knobbe Martens Olson & Bear, LLP (57) ABSTRACT

A method for deriving shape information of a person's skull and dentition, including the steps of: taking an impression of the person's dentition, taking a first scan of the person's head, while the person is wearing the impression, taking a second scan of the impression alone, combining the scans, deriving the shape information from the combined scans. Advantageously the method further includes the step of taking a third scan of the person's head alone without the impression.

23 Claims, 8 Drawing Sheets

(51) Int. Cl.
  *A61B 5/107* (2006.01)
  *A61C 19/05* (2006.01)
  *A61C 9/00* (2006.01)
  *A61B 5/00* (2006.01)
  *A61B 17/66* (2006.01)
  *A61B 17/80* (2006.01)

(52) U.S. Cl.
  CPC ............ *A61C 9/0046* (2013.01); *A61C 19/05* (2013.01); *A61B 5/4504* (2013.01); *A61B 17/666* (2013.01); *A61B 17/80* (2013.01)

(56) References Cited

U.S. PATENT DOCUMENTS

| | | | |
|---|---|---|---|
| 5,066,231 A | 11/1991 | Oxman et al. | |
| 5,338,198 A | 8/1994 | Wu et al. | |
| 5,690,631 A * | 11/1997 | Duncan et al. | 606/281 |
| 5,800,174 A | 9/1998 | Andersson | |
| 5,851,115 A | 12/1998 | Carlsson et al. | |
| 5,975,893 A | 11/1999 | Chishti et al. | |
| 6,015,289 A | 1/2000 | Andreiko et al. | |
| 6,049,743 A | 4/2000 | Baba | |
| 6,068,482 A | 5/2000 | Snow | |
| 6,099,314 A | 8/2000 | Kopelman et al. | |
| 6,120,289 A * | 9/2000 | Cleary et al. | 433/22 |
| 6,152,731 A | 11/2000 | Jordan et al. | |
| 6,206,693 B1 | 3/2001 | Hultgren | |
| 6,217,325 B1 | 4/2001 | Chishti et al. | |
| 6,217,334 B1 | 4/2001 | Hultgren | |
| 6,227,850 B1 | 5/2001 | Chishti et al. | |
| 6,261,098 B1 | 7/2001 | Persson | |
| 6,318,994 B1 | 11/2001 | Chishti et al. | |
| 6,322,359 B1 | 11/2001 | Jordan et al. | |
| 6,371,761 B1 | 4/2002 | Cheang et al. | |
| 6,386,878 B1 | 5/2002 | Pavlovskaia et al. | |
| 6,398,548 B1 | 6/2002 | Muhammad et al. | |
| 6,406,292 B1 | 6/2002 | Chishti et al. | |
| 6,450,807 B1 | 9/2002 | Chishti et al. | |
| 6,457,972 B1 | 10/2002 | Chishti et al. | |
| 6,463,344 B1 | 10/2002 | Pavloskaia et al. | |
| 6,471,511 B1 | 10/2002 | Chishti et al. | |
| 6,551,611 B2 | 4/2003 | Elliesen et al. | |
| 6,579,095 B2 | 6/2003 | Marshall et al. | |
| 6,582,229 B1 | 6/2003 | Miller et al. | |
| 6,602,070 B2 | 8/2003 | Miller et al. | |
| 6,626,666 B2 | 9/2003 | Chishti et al. | |
| 6,629,840 B2 | 10/2003 | Chishti et al. | |
| 6,633,789 B1 | 10/2003 | Nikolskiy et al. | |
| 6,640,130 B1 * | 10/2003 | Freeman | A61B 5/0059 382/128 |
| 6,640,150 B1 | 10/2003 | Persson et al. | |
| 6,665,570 B2 | 12/2003 | Pavloskaia et al. | |
| 6,682,346 B2 | 1/2004 | Chishti et al. | |
| 6,685,469 B2 | 2/2004 | Chishti et al. | |
| 6,688,886 B2 | 2/2004 | Hughes et al. | |
| 6,697,164 B1 | 2/2004 | Babayoff et al. | |
| 6,699,037 B2 | 3/2004 | Chishti et al. | |
| 6,722,880 B2 | 4/2004 | Chishti et al. | |
| 6,726,478 B1 | 4/2004 | Isiderio et al. | |
| 6,729,876 B2 | 5/2004 | Chishti et al. | |
| 6,730,091 B1 * | 5/2004 | Pfefferle et al. | 606/70 |
| 6,767,208 B2 | 7/2004 | Kaza | |
| 6,783,360 B2 | 8/2004 | Chishti | |
| 6,786,721 B2 | 9/2004 | Chishti et al. | |
| 6,802,713 B1 | 10/2004 | Chishti et al. | |
| 6,940,611 B2 | 9/2005 | Babayoff et al. | |
| 6,948,936 B2 | 9/2005 | Miller et al. | |
| 6,960,211 B1 * | 11/2005 | Pfefferle et al. | 606/282 |
| 6,979,196 B2 | 12/2005 | Nikolskiy et al. | |
| 7,030,383 B2 | 4/2006 | Babayoff et al. | |
| 7,040,896 B2 | 5/2006 | Pavloskaia et al. | |
| 7,074,038 B1 | 7/2006 | Miller | |
| 7,092,107 B2 | 8/2006 | Babayoff et al. | |
| 7,092,784 B1 | 8/2006 | Simkins | |
| 7,101,178 B2 | 9/2006 | Diesso | |
| 7,118,375 B2 | 10/2006 | Durbin et al. | |
| 7,134,874 B2 | 11/2006 | Chishti et al. | |
| 7,140,877 B2 | 11/2006 | Kaza | |
| 7,140,887 B2 | 11/2006 | Poh et al. | |
| 7,145,661 B2 | 12/2006 | Hitzenberger | |
| 7,160,110 B2 | 1/2007 | Imgrund et al. | |
| 7,202,466 B2 | 4/2007 | Babayoff et al. | |
| 7,214,946 B2 | 5/2007 | Babayoff et al. | |
| 7,220,122 B2 | 5/2007 | Chishti | |
| 7,230,725 B2 | 6/2007 | Babayoff et al. | |
| 7,241,142 B2 | 7/2007 | Abolfathi et al. | |
| 7,252,507 B2 | 8/2007 | Tesini | |
| 7,255,558 B2 | 8/2007 | Babayoff et al. | |
| 7,273,367 B2 | 9/2007 | Hughes et al. | |
| 7,286,954 B2 | 10/2007 | Kopelman et al. | |
| 7,319,529 B2 | 1/2008 | Babayoff | |
| 7,320,592 B2 | 1/2008 | Chishti et al. | |
| 7,326,051 B2 | 2/2008 | Miller | |
| 7,331,783 B2 | 2/2008 | Chishti et al. | |
| 7,333,874 B2 | 2/2008 | Taub et al. | |
| 7,347,690 B2 | 3/2008 | Jordan et al. | |
| 7,357,634 B2 | 4/2008 | Knopp | |
| 7,361,020 B2 | 4/2008 | Abolfathi et al. | |
| 7,362,890 B2 | 4/2008 | Scharlack et al. | |
| 7,373,286 B2 | 5/2008 | Nikolskiy et al. | |
| 7,377,778 B2 | 5/2008 | Chishti et al. | |
| 7,428,481 B2 | 9/2008 | Nikolskiy et al. | |
| 7,433,810 B2 | 10/2008 | Pavloskaia et al. | |
| 7,435,083 B2 | 10/2008 | Chishti et al. | |
| 7,442,040 B2 | 10/2008 | Kuo | |
| 7,452,207 B2 | 11/2008 | Miller et al. | |
| 7,474,307 B2 | 1/2009 | Chishti et al. | |
| 7,476,100 B2 | 1/2009 | Kuo | |
| 7,477,402 B2 | 1/2009 | Babayoff et al. | |
| 7,511,829 B2 | 3/2009 | Babayoff | |
| 7,536,234 B2 | 5/2009 | Kopelman et al. | |
| 7,547,873 B2 | 6/2009 | Babayoff et al. | |
| 7,555,403 B2 | 6/2009 | Kopelman et al. | |
| 2001/0002310 A1 | 5/2001 | Chishti et al. | |
| 2001/0006770 A1 | 7/2001 | Chishti et al. | |
| 2001/0008751 A1 | 7/2001 | Chishti et al. | |
| 2001/0009753 A1 | 7/2001 | Chishti et al. | |
| 2002/0064747 A1 | 5/2002 | Chishti et al. | |
| 2002/0064748 A1 | 5/2002 | Chishti et al. | |
| 2002/0094509 A1 | 7/2002 | Durbin et al. | |
| 2002/0119423 A1 | 8/2002 | Chishti et al. | |
| 2002/0150855 A1 | 10/2002 | Shishti et al. | |
| 2002/0177108 A1 | 11/2002 | Pavlovskaia et al. | |
| 2003/0003416 A1 | 1/2003 | Chishti et al. | |
| 2003/0008259 A1 | 1/2003 | Kuo et al. | |
| 2003/0009252 A1 | 1/2003 | Pavlovskaia et al. | |
| 2003/0064345 A1 | 4/2003 | Chishti et al. | |
| 2003/0139834 A1 | 7/2003 | Nikolskiy et al. | |
| 2003/0198917 A1 | 10/2003 | Miller et al. | |
| 2003/0207227 A1 | 11/2003 | Abolfathi | |
| 2003/0232302 A1 | 12/2003 | Babayoff et al. | |
| 2003/0235803 A1 | 12/2003 | Nikolskiy et al. | |
| 2004/0023183 A1 | 2/2004 | Miller et al. | |
| 2004/0023188 A1 | 2/2004 | Pavlovskaia et al. | |
| 2004/0090638 A1 | 5/2004 | Babayoff et al. | |
| 2004/0096799 A1 | 5/2004 | Hughes et al. | |
| 2004/0110110 A1 | 6/2004 | Chishti et al. | |
| 2004/0128010 A1 | 7/2004 | Pavlovskaia et al. | |
| 2004/0137400 A1 | 7/2004 | Chishti et al. | |
| 2004/0137408 A1 | 7/2004 | Embert et al. | |
| 2004/0166456 A1 | 8/2004 | Chishti et al. | |
| 2004/0170941 A1 | 9/2004 | Phan et al. | |
| 2004/0170943 A1 | 9/2004 | Chishti et al. | |
| 2004/0172150 A1 | 9/2004 | Perot et al. | |
| 2004/0175671 A1 | 9/2004 | Jones et al. | |
| 2004/0191719 A1 | 9/2004 | Kaza | |
| 2004/0197740 A1 | 10/2004 | Amar | |
| 2004/0224286 A1 | 11/2004 | Kaza et al. | |
| 2004/0241606 A1 | 12/2004 | Diesso | |
| 2004/0243361 A1 | 12/2004 | Steuben et al. | |
| 2004/0259051 A1 | 12/2004 | Brajnovic | |
| 2005/0019721 A1 | 1/2005 | Chishti | |
| 2005/0026102 A1 | 2/2005 | Miller | |
| 2005/0048432 A1 | 3/2005 | Choi et al. | |

(56) References Cited

U.S. PATENT DOCUMENTS

| | | |
|---|---|---|
| 2005/0055118 A1 | 3/2005 | Nikolskiy et al. |
| 2005/0079468 A1 | 4/2005 | Chishti et al. |
| 2005/0080328 A1 | 4/2005 | Vass et al. |
| 2005/0106528 A1 | 5/2005 | Abolfathi et al. |
| 2005/0106529 A1 | 5/2005 | Abolfathi et al. |
| 2005/0159522 A1* | 7/2005 | Bublewitz ............... C08L 83/04 524/430 |
| 2005/0186524 A1 | 8/2005 | Abolfathi et al. |
| 2005/0191593 A1 | 9/2005 | Knopp |
| 2005/0192835 A1 | 9/2005 | Kuo et al. |
| 2005/0196724 A1 | 9/2005 | Miller et al. |
| 2005/0208449 A1 | 9/2005 | Abolfathi et al. |
| 2005/0244782 A1 | 11/2005 | Chishti et al. |
| 2005/0264828 A1 | 12/2005 | Babayoff et al. |
| 2006/0003292 A1 | 1/2006 | Lauren et al. |
| 2006/0097178 A1 | 5/2006 | Babayoff et al. |
| 2006/0158665 A1 | 7/2006 | Babayoff et al. |
| 2006/0212260 A1 | 9/2006 | Kopelman et al. |
| 2006/0263738 A1 | 11/2006 | Kuo |
| 2006/0275736 A1 | 12/2006 | Wen et al. |
| 2006/0286501 A1 | 12/2006 | Chishti et al. |
| 2007/0003907 A1 | 1/2007 | Chishti et al. |
| 2007/0031791 A1 | 2/2007 | Cinader et al. |
| 2007/0092850 A1 | 4/2007 | Kaza |
| 2007/0109559 A1 | 5/2007 | Babayoff et al. |
| 2007/0128573 A1 | 6/2007 | Kuo |
| 2007/0128574 A1 | 6/2007 | Kuo et al. |
| 2007/0129991 A1 | 6/2007 | Kuo |
| 2007/0134613 A1 | 6/2007 | Kuo et al. |
| 2007/0134617 A1 | 6/2007 | Babayoff et al. |
| 2007/0141527 A1 | 6/2007 | Kuo et al. |
| 2007/0145248 A1 | 6/2007 | Babayoff et al. |
| 2007/0164203 A1 | 7/2007 | Babayoff et al. |
| 2007/0168152 A1* | 7/2007 | Matov .................... A61C 7/00 702/155 |
| 2007/0190481 A1* | 8/2007 | Schmitt .................... 433/68 |
| 2007/0197902 A1 | 8/2007 | Schutyser |
| 2007/0203663 A1 | 8/2007 | Kopelman et al. |
| 2007/0238065 A1 | 10/2007 | Sherwood et al. |
| 2008/0002869 A1 | 1/2008 | Scharlack et al. |
| 2008/0015727 A1 | 1/2008 | Dunne et al. |
| 2008/0024768 A1 | 1/2008 | Babayoff |
| 2008/0038684 A1 | 2/2008 | Keating et al. |
| 2008/0038688 A1 | 2/2008 | Kopelman et al. |
| 2008/0057466 A1 | 3/2008 | Jordan et al. |
| 2008/0064008 A1* | 3/2008 | Schmitt .................... 433/140 |
| 2008/0085487 A1 | 4/2008 | Kuo et al. |
| 2008/0131832 A1 | 6/2008 | Miller |
| 2008/0131841 A1 | 6/2008 | Taub et al. |
| 2008/0159608 A1 | 7/2008 | Suetens et al. |
| 2008/0166676 A1 | 7/2008 | Chishti et al. |
| 2008/0182220 A1 | 7/2008 | Chishti et al. |
| 2008/0182221 A1 | 7/2008 | Chishti et al. |
| 2008/0187879 A1 | 8/2008 | Chishti et al. |
| 2008/0206705 A1 | 8/2008 | Kaza et al. |
| 2008/0248443 A1 | 10/2008 | Chishti et al. |
| 2008/0259411 A1 | 10/2008 | Karlsson |
| 2008/0268400 A1 | 10/2008 | Moss et al. |
| 2008/0288289 A1 | 11/2008 | Sah |
| 2008/0300716 A1 | 12/2008 | Kopelman et al. |
| 2008/0305452 A1 | 12/2008 | Sterental et al. |
| 2008/0305453 A1 | 12/2008 | Kitching et al. |
| 2008/0306724 A1 | 12/2008 | Kitching et al. |
| 2008/0316209 A1 | 12/2008 | Wen |
| 2009/0148807 A1 | 6/2009 | Babayoff et al. |
| 2009/0148809 A1 | 6/2009 | Kuo et al. |
| 2009/0153858 A1 | 6/2009 | Babayoff |
| 2009/0153879 A1 | 6/2009 | Babayoff et al. |
| 2009/0191502 A1 | 7/2009 | Cao et al. |
| 2009/0191503 A1 | 7/2009 | Matov et al. |
| 2009/0246726 A1 | 10/2009 | Chelnokov et al. |
| 2009/0286196 A1 | 11/2009 | Wen et al. |
| 2009/0316966 A1* | 12/2009 | Marshall ............... A61B 6/5217 382/128 |

FOREIGN PATENT DOCUMENTS

| | | | |
|---|---|---|---|
| EP | 2368498 A1 * | 9/2011 | |
| JP | 2005-161053 | 6/2005 | |
| JP | 2005-261440 | 9/2005 | |
| JP | 2006-051359 | 2/2006 | |
| JP | 2006-506153 | 2/2006 | |
| JP | 2006-512960 | 4/2006 | |
| JP | 2007-061592 | 3/2007 | |
| JP | 2007-509033 | 4/2007 | |
| WO | WO 99/59106 | 11/1999 | |
| WO | WO 03/028577 | 4/2003 | |
| WO | WO 03028577 A2 * | 4/2003 | ......... A61B 17/6433 |
| WO | WO 2004/047025 | 6/2004 | |
| WO | WO 2004/063990 | 7/2004 | |
| WO | WO 2005/094436 | 10/2005 | |
| WO | WO 2006/000063 | 1/2006 | |
| WO | WO 2007/011314 | 1/2007 | |
| WO | WO 2007/026598 | 3/2007 | |

OTHER PUBLICATIONS

"Medical Image Registration" by J. Michael Fitzpatrick from the Dept of Electrical Engineering and Computer Science at Vanderbilt Univertiy, Nashville, TN—Published on Nov. 3, 2008—http://bluecoat-02/?cfru=aHR0cDovL2VIY3MudmFuZGVyYmlsdC5I ZHUvcGVvcGxIL21pa2VmaXRzcGF0cmljay9mcmllbmRzL252cm EvaWV3LnBwdA==.*

"Medical Image Registration" by J. Michael Fitzpatrick from the Dept of Electrical Engineering and Computer Science at Vanderbilt Univertiy, Nashville, TN—Published on Nov. 3, 2008—http://bluecoat-02/?cfru=aHR0cDovL2VIY3MudmFuZGVyYmlssd C5IZHUvcGVvcGxIL21pa2VmaXRzcGF0cmljay9mcmllbmRzcn MvcmVuaXN0cmF0aW9uX292ZXJ2aWV3LnBwdA==.*

"Medical Image Registration" by J. Michael Fitzpatrick from the Dept of Electrical Engineering and Computer Science at Vanderbilt Univertiy, Nashville, TN—Published on Nov. 3, 2008—http://bluecoat-02/?cfru=aHR0cDovL2VIY3MudmFuZGVyYmlsdC5I ZHUvcGVvcGxIL21pa2VmaXRzcGF0cmljay9mcmllbmRzL252cm EvaWV3LnBwdA==.*

Schutyser et al., "Robust Visualization of the Dental Occlusion by a Double Scan Procedure," MICCAI 2005, pp. 368-374, LNCS 3749, Springer-Verlag, Berlin Heidelberg.

Verstreken et al., "A Double Scanning Procedure for Visualisation of Radiolucent Objects in Soft Tissues: Application to Oral Implant Surgery Planning," MICCAI 1998, pp. 985-995, LNCS 1496, Springer-Verlag, Berlin Heidelberg.

International Search Report for International Application No. PCT/EP2008/003135, mailed on Feb. 4, 2009, in 3 pages.

International Preliminary Report on Patentability and Written Opinion for International Application No. PCT/EP2008/003135, issued on Oct. 20, 2009, in 7 pages.

Extended European Search Report for European Patent Application No. 07106650.0 dated Nov. 9, 2007, in 8 pages.

Maes, et al. "Multimodality image registration by maximilization of mutual information". IEEE Transaction on Medical Imageing, vol. 16, No. 2, pp. 187-198.

Omura, et al., "Two Cases of Skeletal Class II Maklocclussion with Sever Osteoerthrosis of TMJs Treated by Orthognatic Surgery". The Japanese Society for Jaw Deformities, Japan, vol. 16, No. 1, p. 23-32. Apr. 2006.

Japanese Office Action, dated Jul. 17, 2015.

* cited by examiner

Fig. 12D

METHOD FOR DERIVING SHAPE INFORMATION

RELATED APPLICATIONS

This application is a U.S. National Phase of International Application No.: PCT/EP2008/003135, filed Apr. 18, 2008, designating the U.S. and published in English on Oct. 30, 2008 as WO 2008/128720, which claims the benefit of European Application No. 07106650.0, filed Apr. 20, 2007.

FIELD OF THE INVENTION

The present invention relates to methods for assessing the shape of the skull and dentition that are applicable in the field of orthognathic surgery.

BACKGROUND OF THE INVENTION

In maxillofacial surgery, the skull and dentition is surgically remodeled or restored. This surgical discipline encompasses surgical interventions of repair, in particular, of a mis-positioning of the jaws with respect to one another, called orthognathic surgery. Typically, orthognathic surgery involves osteotomies of the maxilla and/or mandible to reposition these bone fragments correctly with respect to the rest of the skull and to create a good occlusion. Osteotomies are surgical operations whereby a bone is cut to shorten, lengthen or change its alignments. With 'occlusion' is meant the manner in which the teeth from upper and lower arches come together when the mouth is closed.

Today's procedure to prepare orthognathic surgery mainly consists of the following steps:
1. Acquisition of 2D cephalograms and performing measurements on them (the latter process is called 'tracing the 2D cephalogram'),
2. Measuring critical distances directly on the patient's face,
3. Taking impressions of the upper and lower dental arch in order to produce plaster casts of the dentition. Taking a wax bite registration in order to relate the plaster casts of the upper and lower dentition in order to know the actual occlusion of the patient and to install the casts in an articulator,
4. Based on the results of step 1 and 2, and on additional information derived of a clinical evaluation of the patient, the plaster models are repositioned in order to optimize the occlusion. The plaster models might be cut during this step.
5. A new facial lateral profile is estimated and drawn on top of the traced 2D cephalogram.
6. An acrylic surgical splint is manually created in order to be able to do the same repositioning of the dental arches during surgery.

With the emergence of 3D technologies, methods to carry out the measurement virtually in three dimensions have been established. As a data input, single or multi-slice CT scans were originally applied. With the emergence of cone-beam CT imaging (CBCT) for dental application, acquisition of 3D scan data becomes common sense in the field.

However, no system is available that visualizes the dentition of the patient in a detailed way using a protocol that is clinically feasible without distorting the facial soft tissues. Such a system would allow detailed occlusion planning possibly even including prediction of soft tissue implication and offer the possibilities to create intra-operative tools to establish the planned solution and to maintain it postoperatively.

WO 2006/000063 describes a method to perform a 3D cephalometric analysis of hard and soft tissues and to derive anatomically relevant movements to reposition bone fragments. It also mentions the possibility to enhance the visualization by fusing a scan of plaster models on the basis of a 3D splint with equipped with at least four markers. An important drawback of said approach is that the 3D splint always disturbs the facial profile.

WO 03/028577 describes a method to generate a surgical splint. The key component in this method is the usage of some markers relative to the patient's dentition identifiable in both the digital dental computer model and the computed tomography computer model to visualize the patient's dentition in detail. The registration method is based on point-based matching. However, this method has as fundamental drawback that the markers are disturbing the natural facial expression during the patient scan. This method to create a visualization of the dentition can be seen as a straightforward extension of the work in the field of dental implant planning (see e.g. 'An image-guided planning system for endosseous oral implants', Verstreken et al., IEEE Trans Med Imaging 1998, 17, pp. 842-852).

U.S. Pat. No. 6,152,731 describes a method for using digital dental models in a digital articulator. It is a digital analogue for the traditional articulator with plaster dental casts. However, this method has as fundamental drawback that the relationship with the anatomy of the patient's head is lost since only the teeth are visible.

AIMS OF THE INVENTION

The present invention aims to provide a method to derive information from an augmented skull model that offers a detailed visualization of the dentition whereby the use of markers is avoided. In a second aspect the invention aims to provide a method for deriving orthognathic planning information. A further aim of the invention is to provide methods for producing intra- and postoperative tools wherein said method to derive information is applied.

SUMMARY OF THE INVENTION

The present invention relates to a method for deriving shape information of a person's skull and dentition, comprising the steps of:
 taking an impression of the person's dentition,
 taking a first scan of the person's head, while the person is wearing the impression,
 taking a second scan of the impression alone,
 combining the scans,
 deriving the shape information from the combined scans.
A major advantage of the method of the present invention is that it is easily applicable in clinical practice and offers the possibility to image the soft tissues in their natural positions. Even more importantly, the method of the invention avoids the need for any fiducial marker (as in WO 03/028577) which yields the substantial advantage that the facial soft tissues are not distorted while performing the method.

Preferably the step of taking the impression is performed with a predefined occlusion.

In a preferred embodiment the method further comprises the step of taking a third scan of the person's head alone without the impression. In that case said step of taking the first scan is performed with a dose less than 45 μSv. The third scan comprises the person's maxillofacial complex. The third scan is taken with a predefined occlusion and facial expression.

Advantageously the second scan is taken with said impression being positioned on a foam-like material. The step of taking the impression is preferably performed with alginate or silicone as impression material. The impression may be taken by means of a wax-bite. In an advantageous embodiment the impression of the person's dentition is a double-sided impression. Preferably the step of taking the impression is performed in a CT scanner.

In a preferred embodiment the method further comprises the step of computing the mandibular autorotation.

In a second aspect the invention relates to a method for deriving orthognathic planning information for repositioning a bone fragment wherein information of a person's skull and dentition is derived with the method as previously described.

The invention further relates to a method for designing and producing an intraoperative splint for transferring a planned occlusion to the surgical field, wherein the splint is designed according to shape information derived from the method as set out above.

The invention also relates to a method for designing and producing a fixation structure for connecting upper and lower dentition, such that a planned occlusion is can be transferred, whereby said fixation structure is designed according to shape information derived from the method for deriving shape information as described. The fixation structure advantageously comprises a set of dental brackets on the lower and upper dentition and a structure for connecting said brackets together in such a way that the planned occlusion is transferred.

In yet another aspect the invention relates to a method for designing and producing customised osteosynthesis plates, designed according to shape information derived from the method as previously described.

The invention further presents a method for designing and producing a postoperative retention tool for preserving a surgically achieved setting, whereby shape information is applied, derived with the method as above described.

The invention also relates to a software program, executable on a programmable device containing instructions, which when executed, perform any of the methods as described.

DETAILED DESCRIPTION OF EMBODIMENT(S)

To plan orthognathic surgery and to perform orthognathic surgery according to the planning three main clinical requirements are obvious:
1. Detailed visualization of the patient's dentition combined with image data of the head and optionally with segmented surfaces out of this image volume. This data set is called an augmented model.
2. Easy and fast planning tool to optimize the occlusion, but also the overall skeletal relationships and soft tissue harmony,
3. Effective intraoperative support to perform surgery as planned.

Possibly postoperative devices to maintain the surgically achieved solution may be needed.

To meet these clinical requirements, technical requirements are derived:
1. Image acquisition protocol allowing for detailed visualization of dentition, optionally without disturbing the soft tissue profile
2. Appropriate tools to move bone fragments into the right occlusion, preserving the skeletal and soft tissue harmony
3. Tools to design and visualize the ideal skin surface for the patient. This ideal skin surface is a target skin surface for simulation. With tools to simulate soft tissue deformation based on bone fragment movements, on soft tissue surgery, on bone fragment sculpting, on implant insertion, etc. . . . , it is checked how well the ideal skin surface can be approximated. Alternatively, movements of bone fragments can be computed to meet the ideal skin surface.

4. Generation of intra-operative tools to perform surgery as planned, and optionally postoperative tools to maintain the surgical result.

Furthermore, economical requirements are defined:

1. The patient handling to obtain the augmented model should be straightforward and fast (this means at least as fast as traditional impression taking and plaster model production and handling),
2. The generation of the surgical (and postsurgical) tools needs to be a (semi-) automatic and cheap procedure.

The present invention features all these requirements.

The proposed image acquisition protocol supports the generation of an augmented model possibly without the soft tissue deformation, without the need to position markers, in a fairly easy and realistic clinical setting. The usage of plaster casts of the patient's dentition is not necessary anymore.

The planning protocol extends the anatomically relevant movements of bone fragments with occlusal planning optimization based on the augmented model. Optionally it includes soft tissue simulation and the design of an ideal 3D soft tissue profile.

Next, these planning results are transferred to the operative field by means of a computer-generated surgical splint, or an anchorage system between the brackets on the upper and lower dental arch, or by customized osteosynthesis plates.

Possibly postoperative tools are generated to preserve the surgical result.

Figure 1:
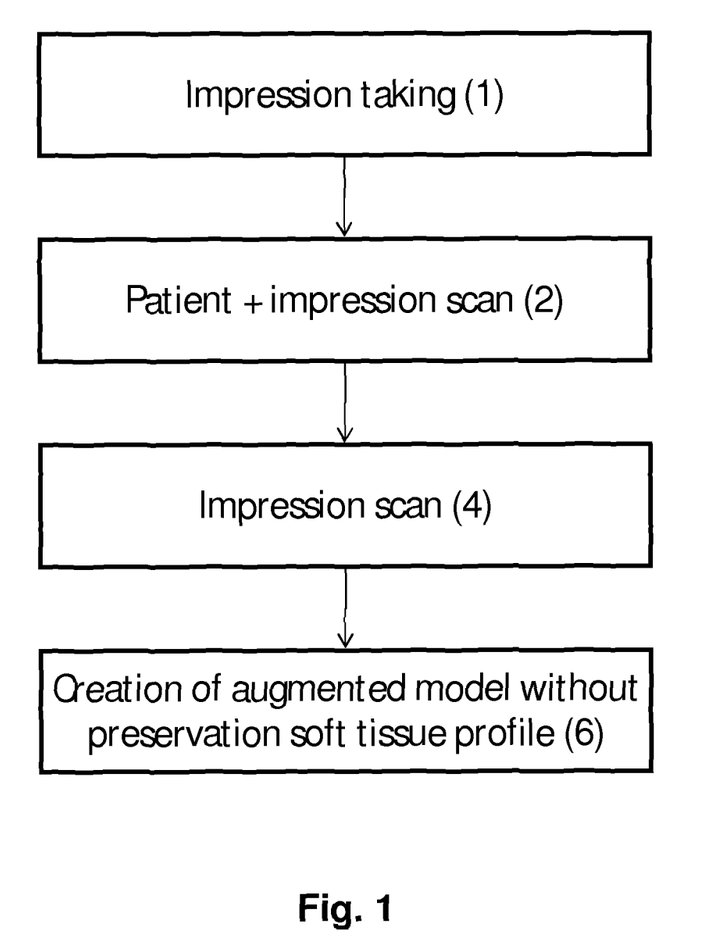
FIG. 1 represents the data flow of the double scan procedure.
Figure 2:
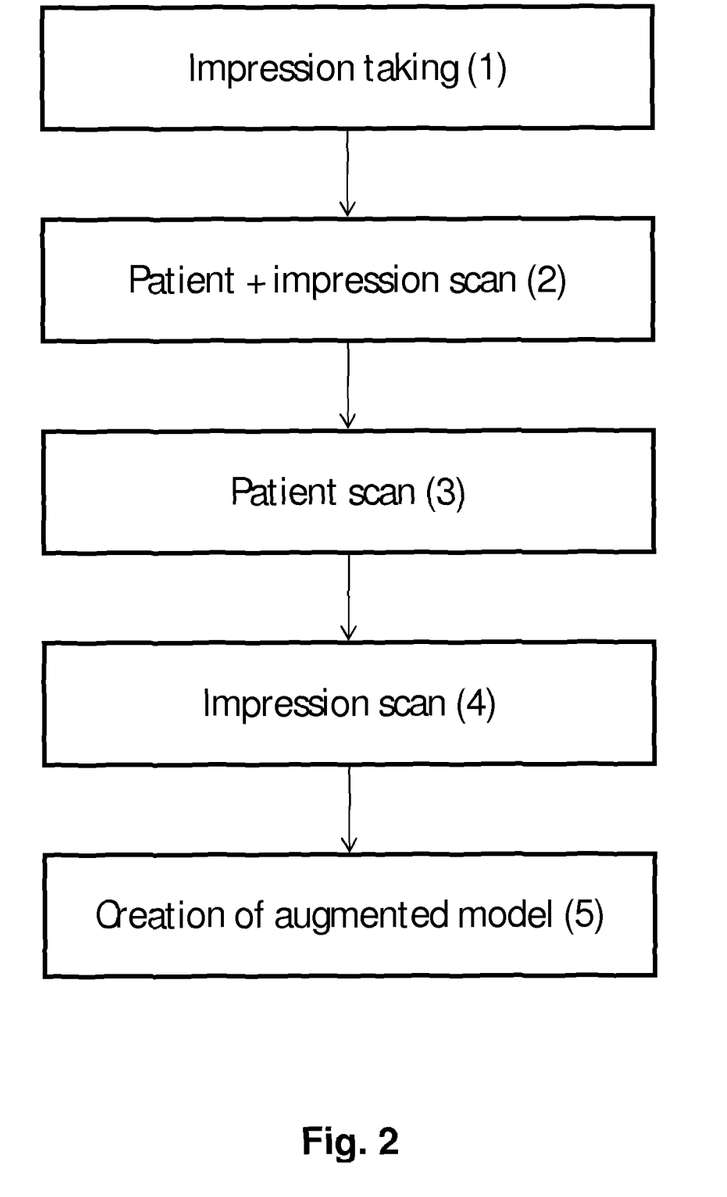
FIG. 2 represents the data flow of the triple scan procedure.
Figure 3A:
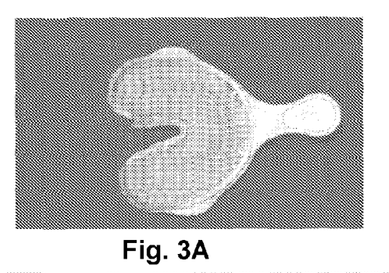
FIG. 3A is a top view an example of a double sided impression.
Figure 3B:
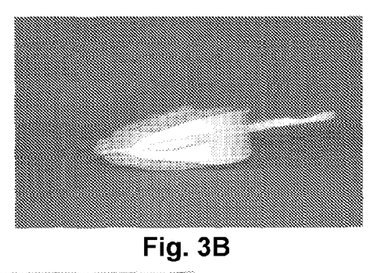
FIG. 3B is a side view an example of a double sided impression.

The patient can be imaged in two ways: without preservation of the soft tissues in natural rest position (the so-called double-scan procedure) (see FIG. 1), or with preservation of the soft tissues in natural rest position (the so-called triple-scan procedure) (see FIG. 2).

Figure 7:
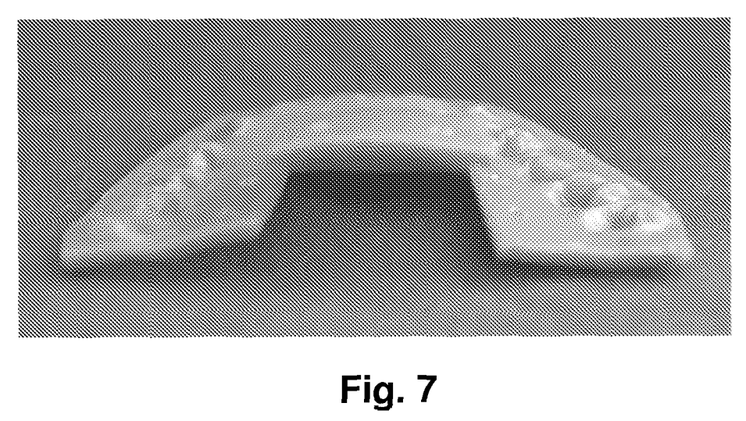
FIG. 7 represents an example of a wax-bite.
Figure 8A:
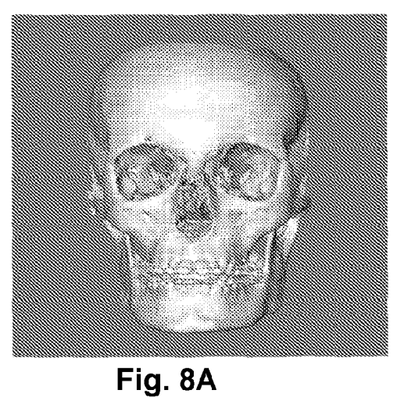
FIG. 8A shows the data of the patient scan.
Figure 8B:
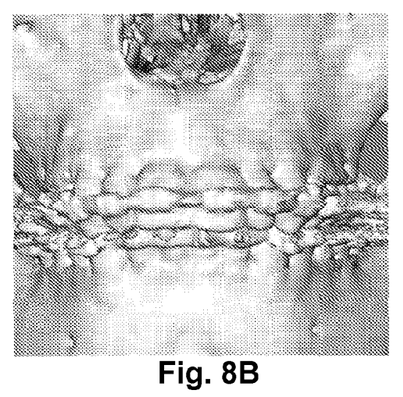
FIG. 8B shows a closer view of the data of the patient scan of FIG. 8A.
Figure 8C:
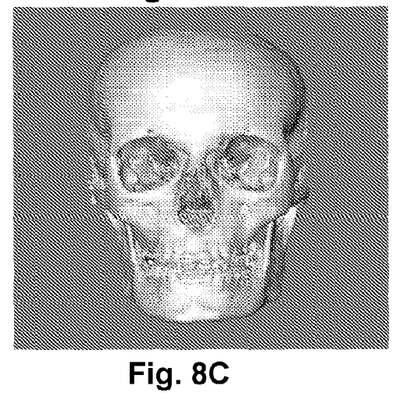
FIG. 8C shows the data of the patient scan with the detailed surface of the dentition.
Figure 8D:
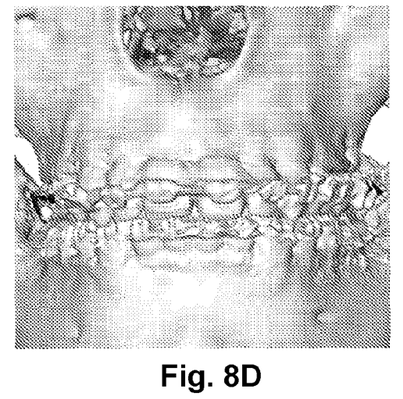
FIG. 8D shows closer view of the data of the patient scan with the detailed surface of the dentition of FIG. 8C.
Figure 8E:
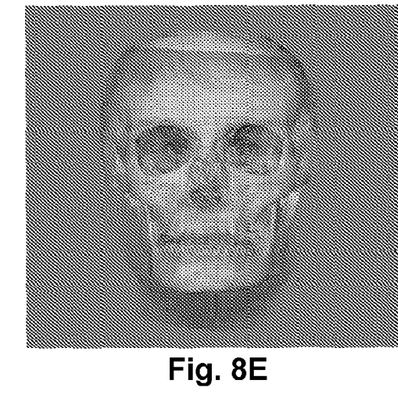
FIG. 8E shows the model of FIG. 8C with the textured skin surface showing the results of an augmented model.
Figure 8F:
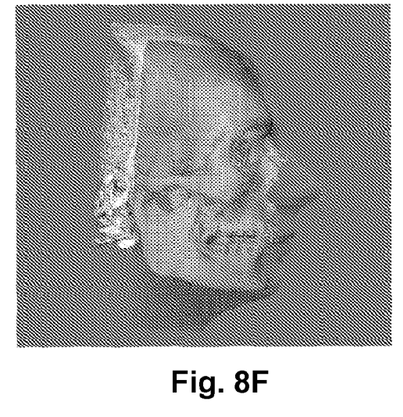
FIG. 8F shows a side view of the model of FIG. 8C with the textured skin surface showing the results of an augmented model.
Figure 9A:
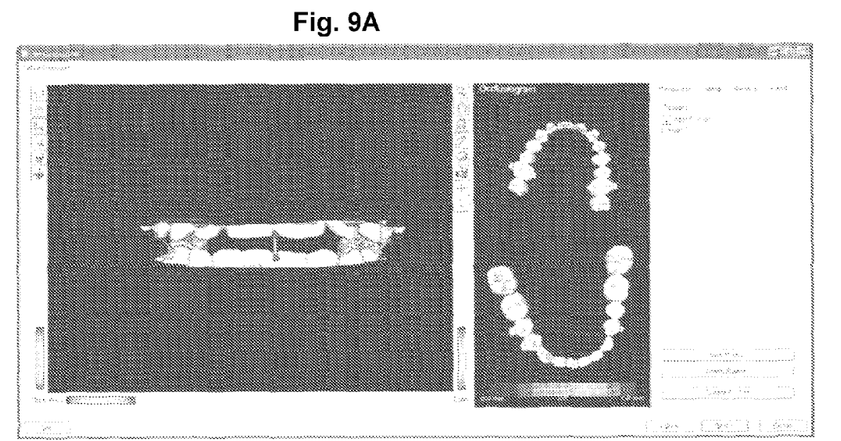
FIG. 9A represents the method to optimize the occlusion by repositioning of the jawbones showing the bone fragments in first position.
Figure 9B:
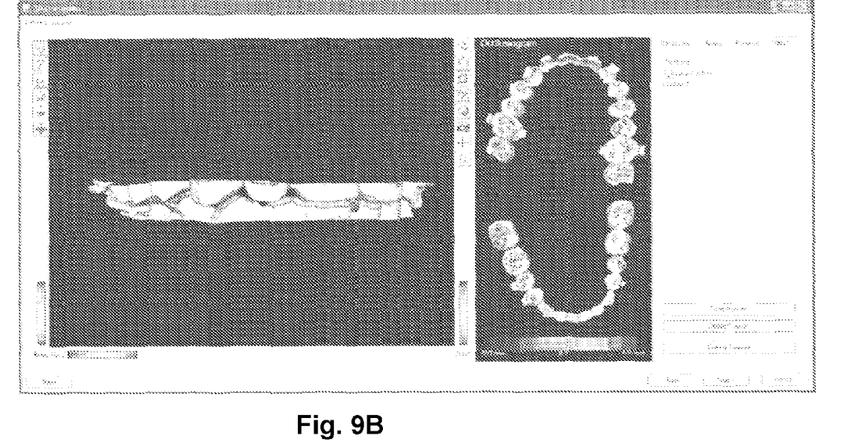
FIG. 9B represents the method to optimize the occlusion by repositioning of the jawbones showing the bone fragments in second position.
Figure 10A:
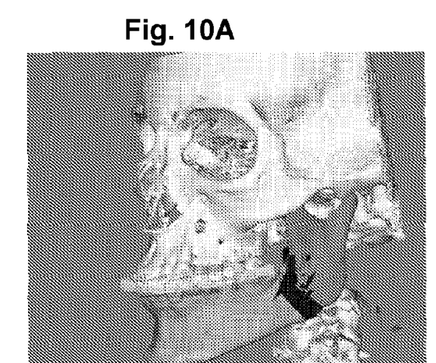
FIG. 10A represents the digital design of a splint based on the planning on the augmented model. An intermediate splint can be designed in a similar way.
Figure 10B:
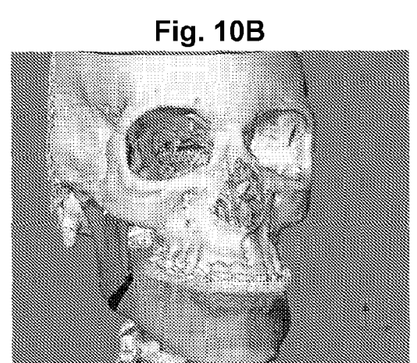
FIG. 10B is another view of a representation the digital design of a splint based on the planning on the augmented model. An intermediate splint can be designed in a similar way.
Figure 10C:
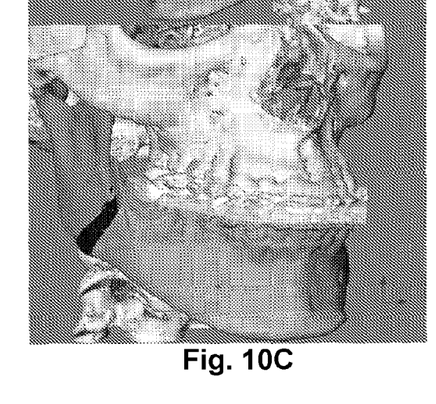
FIG. 10C is another view of a representation of the digital design of a splint based on the planning on the augmented model. An intermediate splint can be designed in a similar way.
Figure 10D:
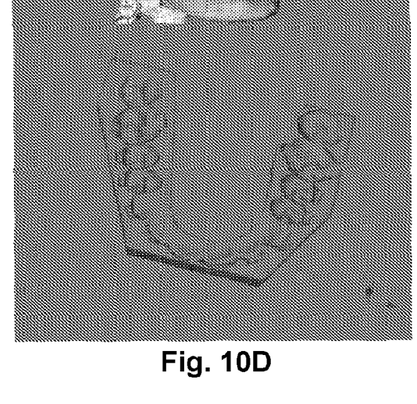
FIG. 10D is a digital representation of a splint based on the digital design of one or more of FIGS. 10A, 10B and 10C.

The double-scan procedure is now described. First an impression of the patient's dentition is produced (see (1) in FIG. 1). Preferably, this impression contains a double-sided impression. It contains the shape information of upper and lower dental arches. As an impression material, all dental impression materials (such as alginate, silicone, . . . among others) or rather thick wax-bites (possibly mixed with barium-sulphate to increase the CT-number (i.e. the gray value)) are applicable. The impression materials can be applied in a double impression tray (see FIG. 3). Wax-bites can be modelled on their own (see FIG. 7). Ideally, the gray values of the impression material are different from those of soft tissues so that the impression can be differentiated from the soft and hard tissues. In the double-scan procedure, it is advantageous that the occlusion of the impression is well controlled and corresponds to the clinically desired occlusion for orthognathic surgery planning.

Next the patient is scanned while wearing the impression (see (2) in FIG. 1). The region of interest of the patient's head is scanned. Ideally, the step of impression taking (step 1 in FIG. 1) is performed in the CT-scanner. In this case, the patient does not need to bite twice in the same impression (as it would be difficult to bite a second time in exactly the same way in the impression). It should be carefully checked that the impression completely covers the cuspids of all teeth.

Figure 5:
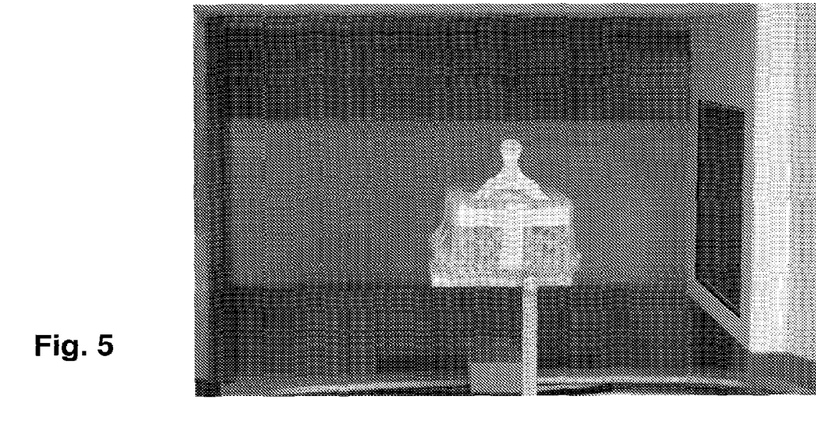
FIG. 5 represents a scan setup for the high resolution scan of the impression.
Figure 6:
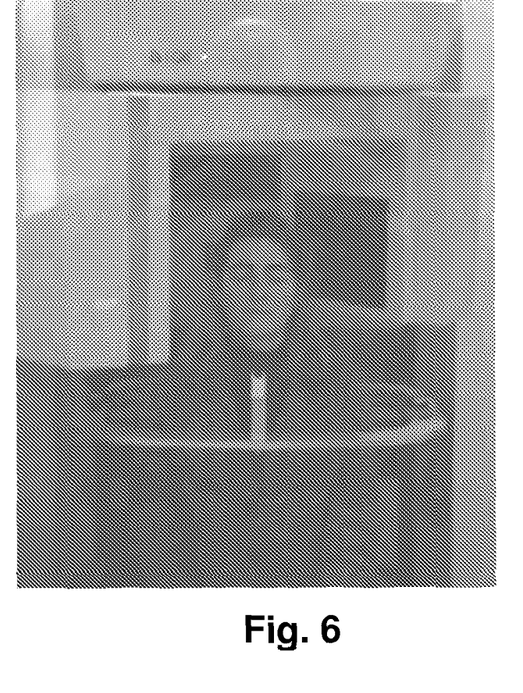
FIG. 6 represents a scan setup for the optional scan of the patient's maxillofacial complex with the occlusion that the doctor wants to examine.

Further, a second high-resolution scan of the impression alone is acquired (see step (4) in FIG. 1 and the illustration in FIG. 5). For reasons of segmentation, the impression should ideally show itself on the CT image data as if it was flying in the air. To accomplish this, the impression can for example be positioned on a foam-like material, such as a sponge.

The various scans are then combined in the following way (step (6) in FIG. 1):

1. Voxel-based rigid registration (i.e. alignment of position and orientation) of the impression scan (4) to the patient+impression scan (2),
2. Image fusion of the detailed impression scan (4) to the maxillofacial complex scan to obtain the augmented model.

Voxel-based rigid registration methods optimize a functional measuring the similarity of all geometrically corresponding voxel pairs for some feature. The voxel-based rigid registration method can be performed by maximization of mutual information, as explained in the paper '*Multimodality image registration by maximization of mutual information*' (Maes et al., IEEE Trans. Medical Imaging, vol. 16, no. 2, pp. 187-198, April 1997).

The image fusion of the scans can be done using surface models extracted from these scans, or within the image volume, or by a combination of both.

In a preferred embodiment the method as set out above comprises an additional step, typically carried out between the steps (2) and (4) of FIG. 1. Step (2) is thereby slightly modified. The data flow scheme of FIG. 2 is then obtained. This is called the triple-scan procedure.

Now during step (1), the occlusion while biting into the impression material is not important and can be randomly chosen. Technically, also single sided impressions could be applied. However this would require an extra patient scan in a further step, which needs to be avoided as much as possible from a clinical point of view.

Figure 4:
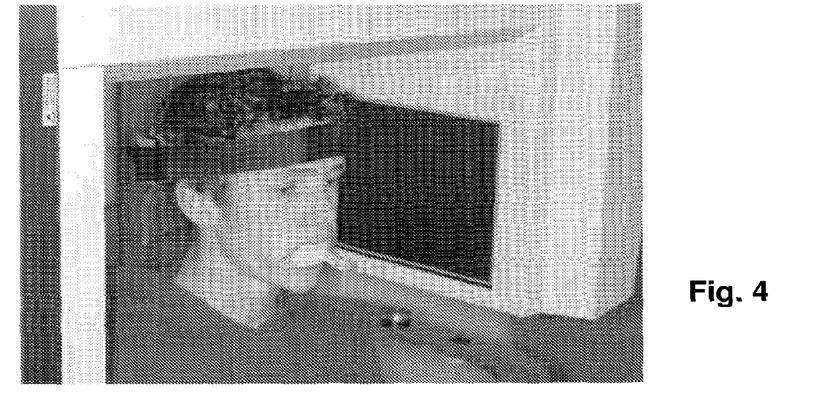
FIG. 4 represents the step of taking a scan of the patient's dentition while he is wearing the impression.

Step 2 is a scan of the patient wearing the impression (see (2) in FIG. 2). A very low dose scan of the dentition is enough (see FIG. 4) given that this scan only yields intermediate results. This very low dose can be understood as less than 45 μSv. Ideally, the step of impression taking (Step 1 in FIG. 2) is performed in the CT-scanner. In this case, the patient does not need to bite twice in the same impression. It should be carefully checked that the impression completely covers the cuspids of all teeth.

In the additional step, the patient is scanned again, but now without the impression (see (3) in FIG. 2). The region of interest of the head is scanned. This is typically the maxillofacial complex. Special attention is paid to the occlusion of the patient and to the facial expression. The occlusion needs to be the occlusion that the doctor wants to examine. This might be controlled by a physician directly during the scan. Alternatively, it can be controlled by a tiny wax bite guiding the patient into the right occlusion. Also the facial expression needs to be the expression that the doctor wants to analyse. Typically this is a central occlusion and a neutral, relaxed facial expression.

Further, a third high-resolution scan of the impression alone is acquired (see step (4) in FIG. 2 and the illustration in FIG. 5) in the same way as step (4) in FIG. 1.

These various scans are then combined in the following way:

1. Voxel-based rigid registration of the impression scan (4) to the patient+impression scan (2), 2. Voxel-based rigid registration of the upper jaw of the patient+impression scan (2) to the upper jaw in the patient scan (3),
3. Voxel-based rigid registration of the lower jaw of the patient+impression scan (2) to the lower jaw in the patient scan (3),
4. Image fusion of the detailed impression scan (4) into the maxillofacial complex scan to obtain the augmented model.

Voxel-based rigid registration methods optimize a functional that measures the similarity of all geometrically corresponding voxel pairs for some feature. The voxel-based rigid registration method can be performed by maximization of mutual information, as already mentioned.

The image fusion of the scans can be done using surface models extracted from these scans, or within the image volume. A combination of both can be envisaged as well.

In the triple-scan procedure, the patient is imaged twice (patient scan and patient+impression scan). In those scans, the patient has a different mouth opening. From these two scans, the rotational axis which defines the movement of the mandible during initial mouth opening and closing can be estimated in the 3D space. This estimated rotational axis can be used for example during the planning of orthognathic surgical procedures: after maxillary impaction surgery the mandible will reposition itself according to this axis. To compute this mandibular movement, first both scans are aligned based on the anatomy of the maxilla. In a second step, the mandible of the second registered scan is aligned with the mandible of the first scan. The alignment can be computed using voxel-based registration, marker-based registration or surface-based registration. The resulting transformation matrix describes the mandibular movement. Out of this transformation matrix, the rotation axis is computed in the 3D space. The initial mouth opening/closing is a rotation around that rotation axis.

As an extra guideline for orthognathic surgery planning, the ideal skin surface based on the current skin surface of the patient can be designed.

A first method to design the ideal skin surface is based on clinical relevant parameters, including functional as well as aesthetic parameters, such as the degree of malocclusion or cephalometric measures, and/or body property parameters (such as body mass index, age, racial properties, gender, etc. . . . ).

A second method to design the ideal skin surface is based on the repositioning of points of the skin surface. These points can be important anatomical landmarks. Based on the new positions of these points, a new skin surface is computed.

As a computational strategy for these methods, a statistical model, based on an extensive database of skin surfaces on a large group of persons, is built. These skin surfaces can be acquired by 3D photography, or extracted from CT or MR imaging. The latter allows also including volumetric data into the statistical model. In this case the relation to the bony structures can also be included in the model. For the first method, the model is parameterized according to said parameters. The initial skin surface is altered according to the changes of the parameter values. For the second method, a statistically relevant skin surface is derived from the initial skin surface adapted according to the repositioned points. Also a combination of both methods is possible.

The ideal skin surface can be set as a target for surgery planning. In order to evaluate how close the surgical plan meets the ideal skin surface, the differences between both surfaces need to be visualised. This can be done by computing a distance map between both surfaces. Ideally, this distance map is based on the distance between anatomically related points. When the differences between both the ideal skin surface and the expected skin surface are minimal, a pleasing surgical plan is obtained.

Orthognathic Surgery Planning

After virtual osteotomies the bone fragments need to be moved to the correct position. Bone fragments are moved with respect to the other skeletal features, to match a desirable occlusion and to obtain an acceptable facial skin surface.

Typically, a bone fragment (e.g. the maxilla) or a group of bone fragments is moved to the appropriate position using anatomical relevant directions, reference planes and anatomical landmarks. Next, bone fragments are moved to optimize the dental occlusion. In the approach according to the present invention, the bone fragments are moved together by spring forces, taking into account the collisions. This technique is called solid body simulation. Finally, further adjustments of the position of bone fragments or groups thereof can be performed.

While doing so, the soft tissue deformation can be simulated and compared with the ideal skin surface.

Intraoperative Tools

To transfer the virtual planning into the surgical field, several approaches are possible. With the intraoperative tools, the planned occlusion can be transferred to the patient. Possibly also the correct position of the bone fragments (like the maxilla) with respect to the skull base and the ascending ramus of the mandible with respect to the TMJ fossa (TMJ means the temporomandibular joint) can be transferred.

Figure 11:
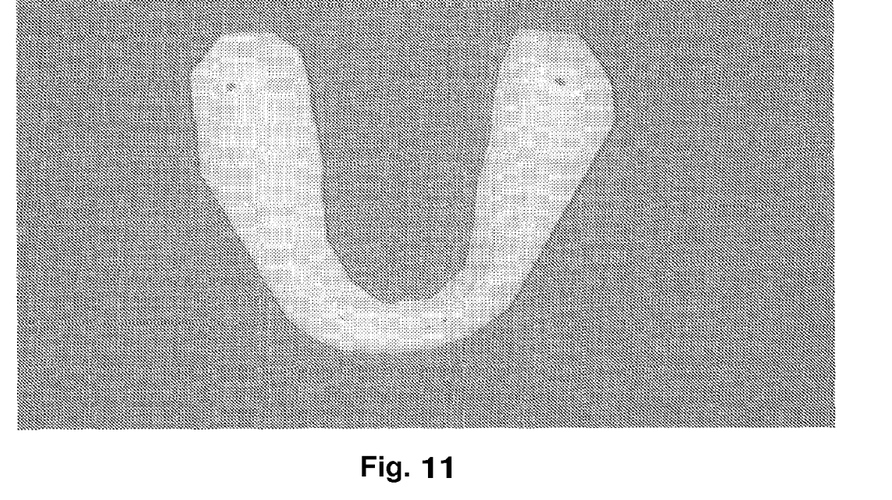
FIG. 11 represents the produced splint for the planning shown in FIG. 10.
Figure 12A:
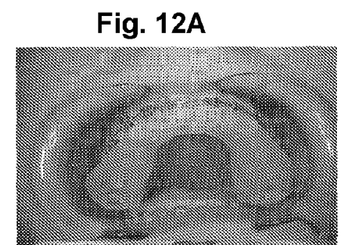
FIG. 12A represents the produced splint for the planning shown in FIG. 10 in a patient's mouth.
Figure 12B:
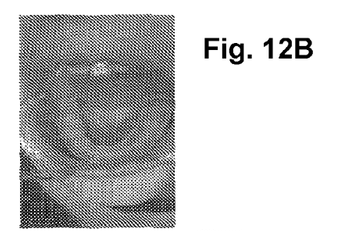
FIG. 12B is another view representing the produced splint for the planning shown in FIG. 10 in a patient's mouth.
Figure 12C:
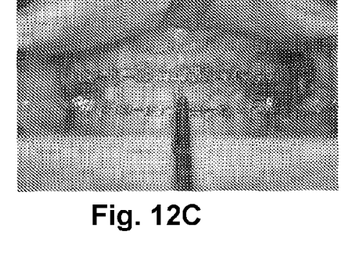
FIG. 12C is another view representing the produced splint for the planning shown in FIG. 10 in a patient's mouth.
Figure 12D:
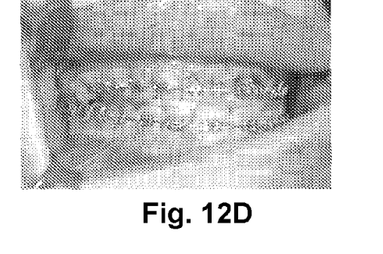
FIG. 12D is another view representing the produced splint for the planning shown in FIG. 10 in a patient's mouth.

A first method to transfer the virtual planning is to produce a surgical splint based on the digital planning data. The splint is designed from the planning data and produced by rapid prototyping techniques or milling techniques (see FIGS. 10, 11 and 12). This method transfers the correct occlusion.

A second method is to produce a fixation structure that connects the upper and lower brackets or the archbars that are wired to the teeth, in order to create the planned occlusion. This method transfers the correct occlusion.

A third method is to produce personalized osteosynthesis plates. When the osteosynthesis plates are in the correct position and the bone fragments are fixed against these plates, the planned bone fragment positions are obtained during surgery. The plates are entered into the correct position based on anatomical features or based on bone anchors that are positioned before patient scanning and segmented from image data obtained from the patient+impression scan in the double-scan method or from the patient scan in the triple-scan method.

Postoperative Tools

In order to stabilize and preserve the surgical result, a postoperative splint might be needed. Also this personalized part can be produced from the results of the planning software.

The advantages of the proposed approach can be summarised as follows. No plaster casts are needed any more, nor the usage of a 3D splint with markers since a different registration concept is applied. This substantially increases the clinical applicability. Moreover, the invention allows having an accurate visualization of the teeth in combination with a natural soft tissue profile, which is a prerequisite to do correct soft tissue deformation prediction.

Also in the field of the planning process, this improved visualization of the teeth enables accurate occlusion planning and the production of intra- and postoperative tools.

Although the present invention has been illustrated by reference to specific embodiments, it will be apparent to those skilled in the art that the invention is not limited to the details of the foregoing illustrative embodiments, and that the present invention may be embodied with various changes and modifications without departing from the spirit and scope thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. In other words, it is contemplated to cover any and all modifications, variations or equivalents that fall within the spirit and scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A method for deriving shape information of a person's skull and dentition without using any fiducial markers, comprising:
   taking an impression of said person's dentition,
   taking a first scan of said person's head, while the person is wearing said impression,
   taking a second scan, via computed tomography (CT) and without use of fiducial markers, of said impression alone outside said person's head,
   combining said scans, whereby a voxel-based rigid registration method is applied to said scans, and
   deriving said shape information from said combined scans.

2. The method for deriving shape information as in claim 1, wherein said taking an impression is performed with a predefined occlusion.

3. The method for deriving shape information as in claim 1, wherein said second scan is taken with said impression being positioned on a foam-like material.

4. The method for deriving shape information as in claim 1, wherein said step of taking an impression is performed with alginate or silicone as impression material.

5. The method for deriving shape information as in claim 1, wherein said taking an impression is performed by means of a wax-bite.

6. The method for deriving shape information as in claim 1, wherein said impression of said person's dentition is a double-sided impression.

7. The method for deriving shape information as in claim 1, wherein said taking an impression is performed in a CT scanner.

8. The method for deriving shape information as in claim 1, further comprising computing the mandibular autorotation.

9. The method for deriving shape information as in claim 1, further comprising taking a third scan of said person's head alone without said impression.

10. The method for deriving shape information as in claim 9, wherein said taking a first scan is performed with a dose less than 45 μSv.

11. The method for deriving shape information as in claim 9, wherein said third scan comprises said person's maxillofacial complex.

12. The method for deriving shape information as in claim 9, wherein said third scan is taken with a predefined occlusion and facial expression.

13. The method for deriving shape information as in claim 1, wherein said first scan is a computed tomography (CT) scan.

14. The method for deriving shape information as in claim 13, wherein said second scan is a computed tomography (CT) scan.

15. A method for deriving shape information of a person's skull and dentition without using any fiducial markers, comprising:
   taking an impression of said person's dentition,
   taking a first scan of said person's head, while the person is wearing said impression,
   taking a second scan, via computed tomography (CT) and without use of fiducial markers, of said impression alone outside said person's head,
   combining said scans, and
   deriving said shape information from said combined scans; and further comprising taking a third scan of said person's head alone without said impression.

16. The method for deriving shape information as in claim 15, wherein said taking a first scan is performed with a dose less than 45 μSv.

17. The method for deriving shape information as in claim 15, wherein said third scan comprises said person's maxillofacial complex.

18. The method for deriving shape information as in claim 15, wherein said third scan is taken with a predefined occlusion and facial expression.

19. The method for deriving shape information as in claim 15, wherein said first scan is a computed tomography (CT) scan.

20. The method for deriving shape information as in claim 19, wherein said second scan is a computed tomography (CT) scan.

21. A method for deriving orthognathic planning information for repositioning a bone fragment, the method comprising:
   taking an impression of a person's dentition;
   taking a first scan of said person's head without using any fiducial markers, while the person is wearing said impression;
   taking a second scan, via computed tomography (CT) and without use of fiducial markers, of said impression alone outside said person's head;
   combining said scans, whereby a voxel-based rigid registration method is applied to said scans;
   deriving, via a programmable device, shape information of said person's skull and dentition from said combined scans; and deriving, via a programmable device, orthognathic planning information for repositioning a bone fragment based at least on the shape information.

22. A method for designing and producing an intraoperative splint for transferring a planned occlusion to a surgical field based on shape information of a person's skull and dentition derived without using any fiducial markers, the method comprising:

taking an impression of a person's dentition;

taking a first scan of said person's head, while the person is wearing said impression;

taking a second scan, via computed tomography (CT) and without use of fiducial markers, of said impression alone outside said person's head;

combining said scans, whereby a voxel-based rigid registration method is applied to said scans;

deriving, via a programmable device, shape information of said person's skull and dentition from said combined scans; and designing, via a programmable device, an intraoperative splint for transferring a planned occlusion to the surgical field, wherein said splint is designed according to the shape information; and producing the intraoperative splint.

23. A program, executable on a programmable device containing instructions, which when executed, derives shape information of a person's skull and dentition without using any fiducial markers, and cause the programmable device to:

receive results of taking a first scan of said person's head, while the person is wearing an impression of said person's dentition;

receive results of taking a second scan, via computed tomography (CT) and without use of fiducial markers, of said impression alone outside said person's head;

combine said scans, whereby a voxel-based rigid registration method is applied to said scans; and derive said shape information from said combined scans.

* * * * *